(12) United States Patent
Goetsch et al.

(10) Patent No.: US 7,388,034 B1
(45) Date of Patent: Jun. 17, 2008

(54) PRODUCTION OF METHANOL FROM THE CRUDE GLYCEROL BY-PRODUCT OF PRODUCING BIODIESEL

(75) Inventors: Duane Goetsch, Andover, MN (US); Ian S. Machay, Eden Prairie, MN (US); Lloyd R. White, Minneapolis, MN (US)

(73) Assignee: G.D.O., Elk River, MN (US)

( * ) Notice: Subject to any disclaimer, the term of this patent is extended or adjusted under 35 U.S.C. 154(b) by 0 days.

(21) Appl. No.: 11/825,018

(22) Filed: Jul. 3, 2007

(51) Int. Cl.
*C07C 27/06* (2006.01)
*C07C 29/151* (2006.01)
*C07C 29/15* (2006.01)

(52) U.S. Cl. .................. 518/703; 518/702; 518/704

(58) Field of Classification Search ............... 518/702, 518/703, 704
See application file for complete search history.

(56) References Cited

U.S. PATENT DOCUMENTS

2007/0225383 A1* 9/2007 Cortright et al. ........... 518/702

* cited by examiner

*Primary Examiner*—Elvis O. Price
(74) *Attorney, Agent, or Firm*—Henry E. Naylor; Kean Miller Hawthorne D'Armond McCowan & Jarman, LLP

(57) ABSTRACT

Production of methanol from a stream of crude glycerol. The crude glycerol is preferably a side product (waste product) that results from the production of biodiesel from vegetable oils and animal fats. The crude glycerol stream is combined with superheated steam and oxygen to produce a synthesis gas that is then passed to a methanol synthesis reaction zone to produce methanol.

18 Claims, 1 Drawing Sheet

PRODUCTION OF METHANOL FROM THE CRUDE GLYCEROL BY-PRODUCT OF PRODUCING BIODIESEL

FIELD OF THE INVENTION

The present invention relates the production of methanol from a stream of crude glycerol. The crude glycerol is preferably a side product (waste product) that results from the production of biodiesel from vegetable oils and animal fats. The crude glycerol stream is combined with superheated steam and oxygen to produce a synthesis gas that is then passed to a methanol synthesis reaction zone to produce methanol.

BACKGROUND OF THE INVENTION

There has been an increasing interest in biodiesel fuels as a supplement to, or replacement for, traditional fossil fuels. The term "biodiesel" is used for a variety of ester-based oxygenated fuels made from vegetable oils, fats, greases, or other sources of triglycerides. It is a nontoxic and biodegradable substitute and supplement for petroleum diesel. Even in blends as low as 20% biodiesel and 80% petroleum diesel (B20), biodiesel can substantially reduce the emission levels and toxicity of diesel exhaust. Biodiesel has been designated as an alternative fuel by the United States Department of Energy and the United States Department of Transportation, and is registered with the United States Environmental Protection Agency as a fuel and fuel additive. It can be used in any diesel engine, without the need for mechanical alterations, and is compatible with existing petroleum distribution infrastructure.

Biodiesel processing involves the production of alkyl esters of long chain fatty acids by reacting the source acid with a low molecular weight alcohol, such as methanol or ethanol. A traditional process for manufacturing fatty acid alkyl esters involves the transesterification of triglycerides using methanol, in the presence of an alkali catalyst. In addition to the desired fatty acid alkyl esters, this process produces an effluent stream comprising glycerol (glycerol), excess alcohol, water, alkyl esters and a mixture of mono, di and triglycerides resulting from the transesterification step. The rapid worldwide expansion of the production of biodiesel fuel since 2000 is creating a rapidly growing supply of byproduct crude glycerol. Over the past year or so the value of crude glycerol has decreased and it is anticipated that biodiesel producers may receive little or no value for this material. A biodiesel plant producing approximately 30,000,000 gallons per year of product generates approximately 22 million pounds of crude glycerol and requires approximately 26 million pounds of methanol (460,000 gallons).

At one time there was a valuable market for glycerol, which assisted the economics of the biodiesel process as a whole. However, with the increase in global biodiesel production, the market price for crude glycerol has crashed. Thus, there is a need in the art for processes capable of converting crude glycerol to more valuable products as well as for reducing the amount of methanol purchased by biodiesel producers from third party sources.

SUMMARY OF THE INVENTION

In accordance with the present invention there is provided a process for producing methanol from crude glycerol, which method comprises:

i) introducing crude glycerol, an effective amount of superheated steam, and an effective amount of oxygen into a reaction zone where the resulting mixture is heated to a temperature of about 1500° F. to about 1900° F. and at pressures from about 200 psig to about 600 psig, thereby resulting in a synthesis gas product stream comprised predominantly of $H_2$ and CO with minor amounts of $CO_2$, and having a temperature substantially that of the reaction zone;

ii) cooling said synthesis gas product stream to a temperature of about 360° F. to about 80° F.;

iii) pressuring the cooled synthesis gas to a pressure of about 500 psig to about 1500 psig thereby resulting in a pressurized cooled synthesis gas;

iv) introducing said pressurized cooled synthesis gas into a methanol synthesis reaction zone along with an effective amount of methanol synthesis catalyst, which methanol synthesis reaction zone is maintained at a temperature from about 300° F. to about 570° F. and pressures from about 500 psig to about 1500 psig, thereby resulting in a methanol synthesis product stream comprised of methanol, water and a tail gas;

v) conducting the methanol synthesis product stream to a first separation zone wherein a tail gas product stream is separated from a liquid product stream, which liquid product stream is comprised of a mixture of methanol and water;

vi) conducting said mixture of methanol and water to a second separation zone wherein substantially all the methanol is separated from the water;

vii) collecting the methanol; and viii) collecting the water.

In a preferred embodiment, the reaction zone is an autothermal reaction zone.

In another preferred embodiment, the product gas stream exiting the reaction zone is cooled in multiple steps.

In another preferred embodiment, the gas exiting the separation zone is further passed to an additional separation zone and passed through a suitable membrane to: 1) produce a hydrogen enriched gas to recycle to the methanol synthesis reactor; and/or 2) reject carbon dioxide.

In another preferred embodiment, an effective amount of steam is added to the pressurized cooled synthesis gas stream being conducted to the methanol reaction zone.

In yet another preferred embodiment, an effective amount of hydrogen is added to the pressurized cooled synthesis gas stream being conducted to the methanol reaction zone.

BRIEF DESCRIPTION OF THE FIGURE

The FIGURE hereof is a simplified flow diagram of a preferred embodiment of the present invention showing process steps for producing methanol from crude glycerol.

DETAILED DESCRIPTION OF THE INVENTION

Figure 1:
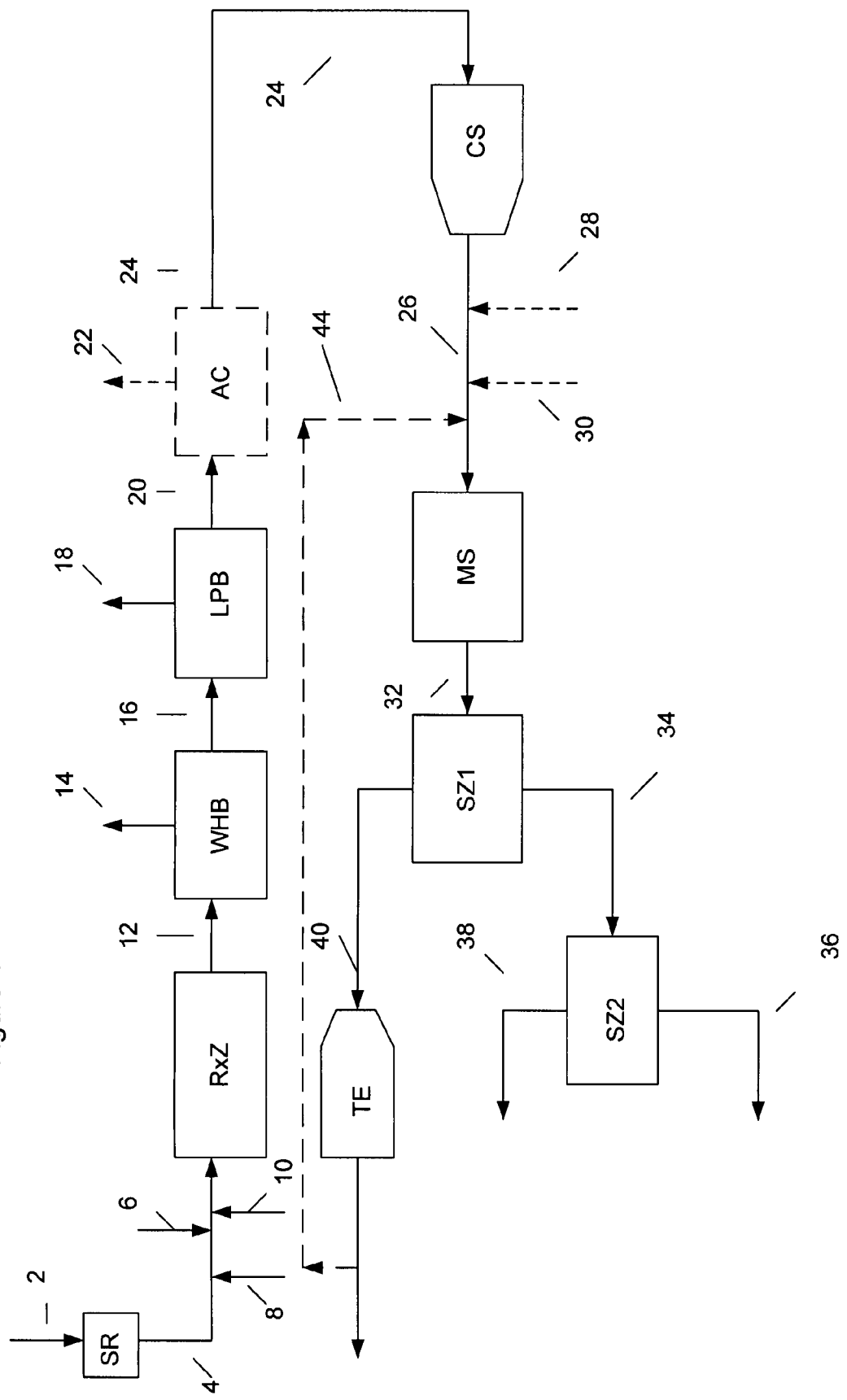

The present invention relates to the conversion of crude glycerol to methanol. Crude glycerol is a by-product produced during the production of biodiesel form vegetable and animal oils and animal fats. It is preferred that the methanol produced by the practice of the present invention be recycled to the biodiesel plant that produced the crude glycerol. It is also preferred that the crude glycerol to methanol process of the present invention be practiced on the same site as a biodiesel plant for economic reasons. The crude glycerol by-product stream from a biodiesel plant is typically comprised of glycerol, methanol, water, inorganic salts (catalyst residue) free fatty acids, unreacted mono-, di-, and triglycerides, methyl esters, as well as a variety of other matter organic non-glycerol (MONG) in varying quantities. The methanol is typically stripped from this stream and recycled, leaving behind, after neutralization, what is known as crude glycerol. In raw form, crude glycerol typically has a high salt and free fatty acid content and substantial color (yellow to dark brown). Consequently, crude glycerol has few direct uses because of the presence of salts and other species, and its fuel value is marginal. The US biodiesel industry generates millions of gallons of crude glycerol by-product each year, and the amount produced is growing rapidly along with the dramatic growth of biodiesel production.

Thus, the combination of high methanol prices, low glycerol prices and the availability of large amounts of by-product crude glycerol have made the present invention commercially attractive for the establishment of small economical methanol production facilities that can be integrated with existing biodiesel plants. The process of the present invention can be scaled to any size biodiesel facility, but it is preferred that the facility be relatively large, for example in excess of 20 million gallons per year of biodiesel production. Power generation can also be added to the process to off-set future costs in electricity.

The process of the present invention can better be understood with reference to the FIGURE hereof which is a simplified process scheme for the production of methanol from crude glycerol, preferably obtained from a biodiesel production facility. A stream of crude glycerol is conducted via line 2 to a salt removal zone SR. The salts to be removed will depend on the particular catalyst used for the production of the biodiesel. For example, if the transesterification zone of the biodiesel process was base catalyzed and if the base was $CH_3ONa$ and neutralized with HCL, then the salt will be NaCl. If the base was $CH_3OK$, then the salt will be KCl. The salt removal zone SR can be comprised of any suitable technology capable of removing salts, such as NaCl and KCl. Non-limiting examples of technologies that can be used in the practice of the present invention for salt removal include vacuum distillation, reverse osmosis, electropherisis, electrodialysis, or a combination thereof. Preferred is electrodialysis. The resulting substantially salt-free glycerol is passed via line 4 to a reaction zone RxZ, which is preferably a gasification zone, more preferably an autothermal reaction zone wherein the crude glycerol is gasified to a synthesis gas. An effective amount of oxygen is also conducted to autothermal reaction zone B via line 6. The oxygen can be obtained from any suitable source, but a preferred source is to produce it on site. This can be done by passing air though a pressure swing adsorption unit (not shown) containing an adsorbent that is more selective for nitrogen then oxygen, thus resulting in an oxygen-rich stream and a nitrogen-rich stream. The oxygen-rich stream is passed to the thermal reforming zone via line 6 and 4 and the nitrogen-rich stream is vented into the atmosphere.

An effective amount of steam is introduced via line 8. It is preferred that the steam be superheated steam. The superheated steam, which will be at a temperature from about 315° C. to about 700° C., acts as both a source of hydrogen as well as to prevent coking. The amount of superheated steam to feedstock will be an effective amount. By effective amount we mean at least that amount needed to prevent coking in the reaction zone RxZ. The ratio of superheated steam to crude glycerol, on a volume to volume basis, will typically be from about 0.2 to 2.5, preferably from about 1.5 to 2.5 and more preferably about 2.2. The mixture of steam and crude glycerol feed will preferably be at a temperature above its dew point, which will typically be greater than about 230° C. It is preferred that an effective amount of an additional organic material (co-feed) be introduced via lines 10 and 4. Non-limiting examples of suitable additional organic materials include free fatty acids, animal fats, oils and organic compounds derived from biomass processing. Preferred are free fatty acids. By effective amount of organic material we mean that amount that will substantially increase the yield of methanol. By substantially increase the yield of methanol we mean at least that amount needed that will result in an increase in the methanol yield by at least about 5 vol. %, more preferably by at least about 10 vol. % over the case where no additional organic material is added. Such an amount can be calculated from the preferred ratio of $H_2$ to CO without producing an undesirable amount of $CO_2$. Non-limiting examples of free fatty acids suitable for use herein include the $C_{14}$ to $C_{20}$ carboxylic acids.

The feed mixture is reacted in reaction zone RxZ at temperatures from about 1500° F. to about 1900° F., preferably from about 1600° C. to about 1800° C. The pressure in reaction zone RxZ will be from about 200 psig to about 600 psig, preferably from about 360 psig to about 440 psig. An autothermal reaction is preferred over other type of reaction zones because in autothermal mode the heating is done directly from products produced during the reaction. That is, once the reaction is initiated with an effective amount of heat, the reaction is self supporting from fuel products resulting from the reaction. Direct heating helps to prevent coking that would more likely result from indirect heating. Within the autothermal reaction zone a combination of partial oxidation, hydrogen reforming, methanation, and a water shift reaction will occur. The autothermal reaction zone is operated adiabatically and the composition of the resulting product gas will be based on the approach to equilibrium. For example, the mole ratios of steam to reduced carbon and oxygen to reduced carbon as well as the amount of oxygen used in the feed will determine the precise composition of the product gas. It is within the scope of this invention that a suitable catalyst be used in reaction zone RxZ which catalyst will typically be a nickel based catalyst. The feed composition to reaction zone RxZ can vary depending on the amount of methanol one wishes to produce in a single pass process and on the amount of carbon in the organic material co-feed, if used. It is desirable to keep the steam/reduced carbon ratios sufficiently high enough to avoid carbon formation. However, the need to produce CO (leads to higher methanol production) limits the maximum value of this ratio. For example, as the concentration of steam is increased, the less likely it will be that coke will form but an increase of $CO_2$ will result with a corresponding decrease in methanol yield. The resulting syngas product will most typically be comprised of about 10-15 vol. % $CO_2$ with the remainder being about a 1:1 ratio of $H_2$:CO.

The product synthesis gas, which is comprised primarily of $H_2$ and CO with minor amounts of $CO_2$, from reaction zone RxZ is cooled to an effective temperature wherein it can be fed to methanol synthesis zone MS. The FIGURE hereof shows multi-step cooling that is preferred to capture as much of the heat energy as possible. For example, the synthesis gas product stream from the reaction zone RxZ is conducted, via line 12 to waste heat boiler WHB wherein high pressure steam 14 is generated which can be utilized for heating requirements at the biodiesel site. It can also be used for supplying heat to other processes, such as crude glycerol cleanup or methanol recovery. The production of high pressure steam requires an exit temperature from the waste heat boiler WHB of about 600° F. or higher. The exit gas from waste heat boiler WHB is passed via line 16 to low pressure boiler LPB which further cools the gas from ≧600° F. to a pressure suitable as low pressure steam (typically between 30 and 150 psig shown by line 18). In one embodiment of the present invention, the cool-down of the product stream can be passed via line 20 to an additional cooling step AC to make extremely low pressure steam, or hot water, while making an intermediate pressure steam in the range of 150 psig (350° F.). This final cooling step AC involves lowering the exit gas temperature to near ambient temperature or at least below about 140° F., in order to reduce the water content prior to subsequent compression. The heat rejected from this final cooling step can be utilized as hot water 22. Some synthesis gas cleanup may be necessary in order to remove any residual solids or unwanted compounds such as sulfur, ammonia, or both. The recovered water can be recycled (not shown) to reaction zone RxZ. Residual solids and unwanted dissolved gases, such as $NH_3$, or possibly other acid gases can be stripped prior to re-use of the water.

The resulting cooled synthesis gas is than conducted via line 24 to compression stage CS. In one embodiment, a $CO_2$ scrubbing stage (not shown) can be utilized to increase the partial pressure of $H_2$ and CO by the removal of at least a portion of any $CO_2$. The pressure of the product gas stream is increased in compression stage CS to at least about1 500 psig, which is necessary in order to achieve a better methanol yield. The resulting compressed synthesis gas stream 26 can be optionally be combined with water, preferably in the form of steam, via line 28 in order to increase the $H_2$ content (through usage of CO) via the shift reaction. The shift step (not shown) can be used in a separate step or part of the overall methanol reactor system. It is optional that hydrogen via line 30 be added to the compressed (pressurized) synthesis gas being conducted to methanol synthesis reactor MS. Methanol synthesis is well known in the art and it is generally performed by passing a synthesis gas comprising hydrogen, carbon oxides and any inert gasses at an elevated temperature and pressure through one or more beds of a methanol synthesis catalyst, which is typically a copper-containing catalyst composition. Methanol is generally recovered by cooling the product gas stream to below the dew point of the methanol and separating the product as a liquid. Preferably, the methanol synthesis reactors are fixed bed reactors with provisions for heat transfer within the catalyst bed(s). Particularly preferred reactors are fixed bed reactors with heat transfer tubes or coils within the catalyst beds. The catalyst may be either inside or outside of the heat transfer tubes, with the cooling fluid on the other side. Multiple cooling tubes can be inside a single reactor. The catalyst bed may also be a fluid bed that is fluidized with a suitable fluid, either gas, liquid, or both. In one embodiment, at least one reactor is a fixed bed reactor having multiple cooling tubes (e.g., coils) spaced within a catalyst bed. In another embodiment, at least one reactor contains multiple tubes, each packed with catalyst, and surrounded by a heat transfer medium.

The catalyst used in the methanol synthesis process is preferably a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc. The methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst. More preferred catalysts for methanol synthesis are those available from Johnson Matthey under the KATALCO 51 Series tradename as well as those available from Haldo-Topsoe under the MK-121 tradename.

The methanol synthesis is performed at pressures in the range of about 40 to about 150 bar absolute, preferably in the range of about 50 to about 120, bar absolute, and more preferably in the range of about 50 to 100 bar absolute. The temperature of the synthesis catalyst is suitably in the range of about 300° to about 570° F., preferably from about 325° to about 500° F., and more preferably from about 350° to about 475° F. The synthesis gas preferably enters the catalyst beds at a temperature in the range of about 200° to about 250° C. and leaves the catalyst beds at temperatures preferably in the range of about 220° to about 260° C. Such temperatures provide for an acceptable methanol output rate (owing to favorable equilibrium) without producing the greater content of by-product impurities, and reduction in catalyst life, that would result from operation at higher temperatures. In a single pass configuration, the catalyst volume is selected to allow near equilibrium conversion. This value is typically in the range of 1500 GHSV with an ideal feed ($H_2$/CO=2.1) with small amounts of $CO_2$ (<10%). Higher concentrations of $CO_2$ and/or lower $H_2$/CO ratios will require larger catalyst volumes.

Returning now to the FIGURE, it is preferred to add hydrogen via line 30 to enhance methanol yields. The product stream from methanol synthesis zone MS is passed via line 32 to first separation zone SZ1, which is preferably a flash drum wherein methanol and water and heavier products, such as dimethylethers, are condensed out. The water/methanol mixture is passed from separation zone SZ1 via line 34 to second separation zone SZ2 which is preferably a distillation zone wherein water and heavy products are separated and collected via line 36. The water can be re-used to produce steam and recycled via line 8. The methanol is collected via line 38 and can be stored, transported, sold or sent to a biodiesel plant. A tail gas stream is collected from first separation zone SZ1 via line 40, which is preferably sent through turboexpander TE that recovers the energy from gas expansion and cools the tail gas. When a turboexpander is used the energy can either be recovered with a shaft coupled electric generator or with a shaft coupled compressor. This minimizes overall energy consumption. The tail gas will typically be comprised of hydrogen and carbon monoxide and can be used for local steam and heating requirement. The tail gas can also be recycled, via line 42, to the methanol synthesis reaction zone, but it is preferred to operate the methanol synthesis reaction zone on a once through basis and the unreacted tail gas used for fuel replacement.

What is claimed is:

1. A process for producing methanol from crude glycerol, which method comprises:
   i) introducing crude glycerol, an effective amount of superheated steam, and an effective amount of oxygen into a reaction zone where the resulting mixture is heated to a temperature of about 1500° F. to about 1900° F. and at pressures from about 200 psig to about 600 psig, thereby resulting in a synthesis gas product stream comprised predominantly of $H_2$ and CO with minor amounts of $CO_2$, and having a temperature substantially that of the reaction zone;

ii) cooling said synthesis gas product stream to a temperature of about 360° F. to about 80° F.;

iii) pressuring the cooled synthesis gas product stream to a pressure of about 500 psig to about 1500 psig thereby resulting in a pressurized cooled synthesis gas product stream;

iv) introducing said pressurized cooled synthesis gas into a methanol synthesis reaction zone along with an effective amount of methanol synthesis catalyst, which methanol synthesis reaction zone is maintained at a temperature from about 300° F. to about 570° F. and pressures from about 500 psig to about 1500 psig, thereby resulting in a methanol synthesis product stream comprised of methanol, water and unreacted syngas tail gas;

v) conducting the methanol synthesis product stream to a first separation zone wherein a tail gas product stream is separated from a liquid product stream, which liquid product stream is comprised of a mixture of methanol and water;

vi) conducting said mixture of methanol and water to a second separation zone wherein substantially all the methanol is separated from the water;

vii) separately collecting the methanol and water.

2. The process of claim 1 wherein the reaction zone is an autothermal reaction zone.

3. The process of claim 1 wherein the catalyst of the methanol synthesis reaction zone is a copper based catalyst.

4. The process of claim 3 wherein the temperature of the methanol synthesis reaction zone is from about 325° F. to about 500° F. and the pressure is from about 50 to about 100 bar absolute.

5. The process of claim 4 wherein the reaction zone is an autothermal reaction zone.

6. The process of claim 1 wherein the first separation zone is flash drum.

7. The process of claim 5 wherein the first separation zone is a flash drum.

8. The process of claim 1 wherein the second separation zone is a distillation zone.

9. The process of claim 7 wherein the second separation zone is a distillation zone.

10. The process of claim 1 wherein an organic material co-feed is introduced in to the reaction zone with the crude glycerol.

11. The process of claim 10 wherein the organic material is selected from the group consisting of free fatty acids, animal fats, oils and organic compounds derived from biomass processing.

12. The process of claim 9 wherein an organic material co-feed is introduced in to the reaction zone with the crude glycerol.

13. The process of claim 12 wherein the organic material is selected from the group consisting of free fatty acids, animal fats, oils and organic compounds derived from biomass processing.

14. The process of claim 1 wherein an effective amount of steam is added to the pressurized cooled synthesis gas.

15. The process of claim 12 wherein an effective amount of steam is added to the pressurized cooled synthesis gas.

16. The process of claim 1 wherein an effective amount of hydrogen is added to the pressurized cooled synthesis gas.

17. The process of claim 15 wherein an effective amount of water is added to the pressurized cooled synthesis gas.

18. The process of claim 1 wherein the tail gas product is recycled to the pressurized cooled synthesis gas.

* * * * *